US009278200B2

(12) United States Patent
Chen (10) Patent No.: US 9,278,200 B2
(45) Date of Patent: Mar. 8, 2016

(54) FLOW CONTROL DEVICE, SYSTEM AND METHOD FOR CONTROLLING THE FLOW OF BODY FLUID

(71) Applicant: Mackay Memorial Hospital, Taipei (TW)

(72) Inventor: Chi-Kuan Chen, Taichung (TW)

(73) Assignee: Mackay Memorial Hospital, Taipei (TW)

( * ) Notice: Subject to any disclaimer, the term of this patent is extended or adjusted under 35 U.S.C. 154(b) by 245 days.

(21) Appl. No.: 14/032,063

(22) Filed: Sep. 19, 2013

(65) Prior Publication Data

US 2014/0081196 A1    Mar. 20, 2014

Related U.S. Application Data

(60) Provisional application No. 61/703,242, filed on Sep. 19, 2012.

(51) Int. Cl.
*A61B 19/00* (2006.01)
*A61M 27/00* (2006.01)

(52) U.S. Cl.
CPC .................. *A61M 27/002* (2013.01)

(58) Field of Classification Search
CPC ............. A61M 27/002; A61M 39/227; A61F 2002/041; A61F 2002/045; A61F 2/04; A61F 5/0079
USPC ............................................................ 604/9
See application file for complete search history.

(56) References Cited

U.S. PATENT DOCUMENTS

| | | | | |
|---|---|---|---|---|
| 5,683,357 A | * | 11/1997 | Magram | 604/8 |
| 6,311,713 B1 | | 11/2001 | Kaartinen | |
| 7,833,186 B1 | * | 11/2010 | Batiste | A61M 1/3655 604/509 |
| 2004/0068221 A1 | * | 4/2004 | Silverberg et al. | 604/9 |
| 2005/0043817 A1 | * | 2/2005 | McKenna et al. | 623/23.65 |
| 2009/0137947 A1 | * | 5/2009 | Yang et al. | 604/66 |
| 2009/0264808 A1 | * | 10/2009 | Young | 604/8 |

* cited by examiner

*Primary Examiner* — Leslie Deak
(74) *Attorney, Agent, or Firm* — Meunier Carlin & Curfman LLC (57) ABSTRACT

Disclosed herein is a device for controlling the flow of a body fluid from a first tissue/organ to a second tissue/organ of a subject. The flow control device includes a main body, a first fluid channel, a second fluid channel, a detection member, and a control member. The main body defines a lumen for accommodating the body fluid flowing from the first tissue/organ into the lumen. The first fluid channel is in fluid communication with the lumen and the first tissue/organ; while the second fluid channel is in fluid communication with the lumen and the second tissue/organ. The detection member is in fluid communication with the lumen, and is operable to detect at least one parameter associated with the flow of the body fluid. The control member is operable to control the flow of the body fluid from the first tissue/organ to the second tissue/organ of the subject.

25 Claims, 8 Drawing Sheets
(1 of 8 Drawing Sheet(s) Filed in Color)

FLOW CONTROL DEVICE, SYSTEM AND METHOD FOR CONTROLLING THE FLOW OF BODY FLUID

CROSS-REFERENCE TO RELATED APPLICATION

This application is a non-provisional patent application of provisional application No. 61/703,242 filed on Sep. 19, 2012, the entirety of which is incorporated herein by reference.

BACKGROUND OF THE INVENTION

1. Field of the Invention

The present disclosure relates to medical methods and devices; and, in particular, to methods and devices for transiently and partially occluding the flow of the body flow in a mammal.

2. Description of Related Art

The body of a living subject contains various types of fluids, and the flow of these body fluids plays an important role in maintaining the functions and overall health of the living subject. Therefore, animal models with a controlled flow of one or more body fluids can be established, allowing for further investigation on disease mechanisms or the function of the body fluid of associated tissue(s)/organ(s). Further, it is also possible to treat diseases or disorders and/or improve the body function by controlling the flow of one or more body fluids.

For example, blood plasma carries blood cells, hormones, proteins, metabolites and other substances throughout the body, and decreased blood flow may cause ischemic tissue damage. However, controlled ischemic condition is also used to treat hypertension or increase dilative capacity. Said controlled ischemic condition could be achieved by transiently occluding and then restoring the blood flow in the blood vessel.

It is also known that the obstruction of pancreatic outflow by cellophane wrapping induces excessive islet neogenesis (also known as nesidioblastosis) that may reverse diabetes. However, this is a potentially dangerous procedure because the extent of islet neogenesis is difficult to control, and may lead to diffuse nesidioblastosis that requires near-total pancreatectomy.

In view of the foregoing, there exists a pressing need for a reliable means (e.g., devices and/or methods) that allows a better control on the flow of a body fluid within a living subject.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a device for controlling the flow of a body fluid from a first tissue/organ to a second tissue/organ of a subject. According to various embodiments of the present disclosure, the flow control device is suitable for transiently and/or partially occluding any vessels or ducts in need of such treatment; illustrative examples of such vessels or duct include, but are not limited to the blood vessel, lymphatic duct, cystic duct, common hepatic duct, common bile duct, pancreatic duct, and salivary gland duct.

According to one embodiment of the present disclosure, the flow control device comprises a main body, a first fluid channel, a second fluid channel, a detection member, and a control member. The main body defines a lumen for accommodating the body fluid flowing from the first tissue/organ into the lumen. The first fluid channel is in fluid communication with the lumen and the first tissue/organ; while the second fluid channel is in fluid communication with the lumen and the second tissue/organ. The first and second fluid channels respectively comprise a proximal end proximal to the main body and a distal end distal to the main body. The detection member is in fluid communication with the lumen, and is operable to detect at least one parameter of the flow rate, velocity, flow resistance and pressure of the body fluid. The control member is operable to control the flow of the body fluid from the first tissue/organ to the second tissue/organ of the subject.

According to one optional embodiment, the body fluid is the pancreatic juice, the first tissue/organ is the pancreas and the second tissue/organ is the duodenum, wherein the distal end of the first fluid channel is connected to the pancreatic duct thereby establishing the fluid communication between the lumen and the pancreas.

Optionally, the first fluid channel may have a plurality of first openings disposed on at least a portion of the surface of the first fluid channel. Alternatively or additionally, the second fluid channel may optionally have a plurality of second openings disposed on at least a portion of the surface of the second fluid channel.

In certain optional embodiments, the diameter of the distal end of the first fluid channel is less than the diameter of the distal end of the second fluid channel.

According to some optional embodiments of the present disclosure, the control member comprises a pump disposed between the first fluid channel and the main body or between the second fluid channel and the main body, in which the pump is operable to provide an output pressure for controlling the flow of the body fluid into and/or from the lumen. Still optionally, the control member may further comprise an adjustment member operatively connected to the pump for adjusting the magnitude of the output pressure of the pump. Alternatively or additionally, the flow control device may further comprise a side fluid channel branching from the first fluid channel and operable to be in fluid communication with the first fluid channel and the lumen.

According to other optional embodiments of the present disclosure, the control member comprises an inflatable balloon and an inflator in fluid communication with the inflatable balloon, in which the inflator is operable to selectively inflate or deflate the inflated balloon, and the inflatable balloon is disposed within the main body such that the flow of the body fluid into and/or from the lumen may be controlled by the level of inflation and/or deflation of the inflatable balloon.

In still some other optional embodiments, the control member comprises at least one pressure valve operable to control the flow of the body fluid into and/or from the lumen. Still optionally, at least one pressure valve is configured to control the inflow of the body fluid from the first fluid channel to the lumen. Alternatively or additionally, at least one pressure valve is optionally configured to control the outflow of the body fluid from the lumen to the second fluid channel. Still alternatively or additionally, at least one pressure valve is configured to control the outflow of the body fluid from the lumen to the detection member according to optional embodiments of the present disclosure. In certain optional embodiments, the flow control device further comprises a sampling unit operable to be in fluid communication with the lumen, and the at least one pressure valve is configured to control the outflow of the body fluid from the lumen to the sampling unit.

In other non-limiting examples of the present disclosure, the control member comprises at least one freeze valve.

According to one example of the present disclosure, the flow control device further comprises at least one multi-way valve that comprises at least two nozzles. In one example, the multi-way valve is a three-way valve that comprises three nozzles. According to optional embodiments of the present disclosure, the multi-way valve is operable to establish the fluid communication between any two of the lumen, the first fluid channel, the second fluid channel and the detection member.

According to optional embodiments of the present disclosure, the flow control device further comprises a third fluid channel operable to be in fluid communication with the lumen and the detection member. Alternatively, the detection member comprises a plurality of sensors disposed within the first fluid channel, the second fluid channel and/or the lumen. For example, the plurality of sensors may comprise thin-film transistors.

In some optional embodiments, the flow control device further comprises at least one tab fixed to the outer surface of the first fluid channel and/or the outer surface of the second fluid channel.

In some optional embodiments, the flow control device further comprises at least one flap extended from the outer surface of the first fluid channel and/or the outer surface of the second fluid channel.

In another aspect, the present disclosure is directed to a system for controlling the flow of a body fluid from a first tissue/organ to a second tissue/organ of a subject. The system could be used to transiently and/or partially occlude and restore the flow of a body fluid from the first tissue/organ to the second tissue/organ via any vessels or ducts.

According to certain embodiments of the present disclosure, the flow control system comprises a flow control device of the above-mentioned aspect/embodiments and a computing device. The computing device is in operative connection with the flow control device, and configured to allow the control member to control the flow of the body fluid from the first tissue/organ to the second tissue/organ of the subject based on a detection result obtained by the detection member.

According to some optional embodiments of the present disclosure, the body fluid is the pancreatic juice, the first tissue/organ is the pancreas and the second tissue/organ is the duodenum. In this case, wherein the distal end of the first fluid channel is connected to the pancreatic duct thereby establishing the fluid communication between the lumen and the pancreas.

In some optional embodiments, the flow control system further comprises a wireless communication module for establishing a communication connection between the flow control device and the computing device.

Still optionally, the computing device comprises a storage unit for storing a set of data of the relationship between an injury level of the first tissue/organ and at least one parameter selected from the group consisting of the flow rate, velocity, flow resistance and pressure of the body fluid; and the control member is operable to control the flow of the body fluid from the first tissue/organ to the second tissue/organ of the subject based on the detection result obtained by the detection member and the set of data.

Alternatively or additionally, the computing device may optionally comprise an analysis unit for analyzing the detection result obtained by the detection member; and the control member is further operable to control the flow of the body fluid from the first tissue/organ to the second tissue/organ of the subject based on the analysis result obtained by the analysis unit.

Alternatively or additionally, the computing device may optionally comprise a determination unit for making a determination based on the detection result obtained by the detection member; and the control member is operable to control the flow of the body fluid from the first tissue/organ to the second tissue/organ of the subject based on the determination result obtained by the determination unit.

According to certain optional embodiments of the present disclosure, the computing device comprises (1) a storage unit for storing a set of data of the relationship between an injury level of the first tissue/organ and at least one parameter selected from the group consisting of the flow rate, velocity, flow resistance and pressure of the body fluid; (2) an analysis unit for analyzing the detection result obtained by the detection member based on the set of data; and (3) a determination unit for making a determination based on the analysis result obtained by the analysis unit; and the control member is operable to control the flow of the body fluid from the first tissue/organ to the second tissue/organ of the subject based on the determination result obtained by the determination unit.

In still another aspect, the present invention is directed to a method for inducing mild inflammation or microinjury in a first and/or second tissue/organ of a subject by controlling the flow of a body fluid from the first tissue/organ to the second tissue/organ of the subject. According to the principles and spirit of the present disclosure, the method uses the flow control device or system according to the above-mentioned aspects/embodiments of the present disclosure to transiently and/or partially occlude and restore the flow of the body fluid within the vessel or duct so as to induce the mild inflammation or microinjury.

According to various embodiments of the present invention, the method comprises the following steps:
(a) arranging the flow control device of claim 1, such that
    (a-1) the distal end of the first fluid channel is adjacent to the exit of the first tissue/organ, thereby allowing the flow of the body fluid from the first tissue/organ into the lumen via the first fluid channel; and (a-2) the distal end of the second fluid channel is connected to an opening of the second tissue/organ, thereby allowing the flow of the body fluid from the lumen into the second tissue/organ via the second fluid channel;
(b) detecting at least one parameter selected from the group consisting of: the flow rate, velocity, flow resistance and pressure of the body fluid by the detection member; and
(c) controlling the flow of the body fluid by the control member such that at least one of the flow rate, velocity, flow resistance and pressure of the body fluid is adjusted to an extent sufficient to cause the mild inflammation or microinjury of the first tissue/organ of the subject.

According to certain optional embodiments of the present disclosure, the body fluid is the pancreatic juice, the first tissue/organ is the pancreas and the second tissue/organ is the duodenum, wherein the distal end of the first fluid channel is connected to the pancreatic duct thereby establishing the fluid communication between the lumen and the pancreas.

According to some optional embodiments of the present disclosure, the subject is a pig, and in step (c) the flow of the pancreatic juice from the pancreas is controlled to an extent such that the pressure within the pancreatic duct is about 10-50 cmH$_2$O.

According to other optional embodiments of the present disclosure, the subject is a human, and in the step (c) the flow of the pancreatic juice from the pancreas is controlled to an extent such that the pressure within the pancreatic duct is about 10-50 cmH$_2$O.

In some optional embodiments, the method further comprises a step (d) of collecting a pancreatic juice or blood sample from the subject, and detecting the level of pancreatic lipase, pancreatic amylase, glucose, insulin or C-peptide of the subject. In this case, the step (c) further comprises adjusting at least one of the flow rate, velocity, flow resistance and pressure of the based on the detection result of the step (d).

In still another aspect, the present invention is directed to a method for inducing neogenesis of endocrine pancreatic tissue and/or exocrine pancreatic tissue in a subject.

According to one embodiment of the present invention, the method comprises transiently and/or partially occluding and restoring the flow of pancreatic juice in the pancreatic duct of the subject such that the transient and/or partial occlusion causes mild pancreatitis or pancreatic microinjury in the subject, thereby inducing the neogenesis of endocrine pancreatic tissue and/or exocrine pancreatic tissue in the subject.

According to the principles and spirit of the present disclosure, the method uses the flow control device or flow control system according to the above-mentioned aspects/embodiments of the present disclosure, and the transient and/or partial occlusion of the pancreatic duct is achieved by the method according to the above mentioned aspect/embodiments of the present disclosure.

In yet another aspect, the present invention is directed to a method for treating diabetes mellitus in a subject.

According to one embodiment of the present invention, the method comprises transiently and/or partially occluding and restoring the flow of the pancreatic juice in the pancreatic duct of the subject such that the partial occlusion causes mild pancreatitis or pancreatic microinjury in the subject, thereby inducing islet neogenesis in the subject to treat diabetes mellitus.

According to the principles and spirit of the present disclosure, the method uses the flow control device or flow control system according to the above-mentioned aspects/embodiments of the present disclosure, and the transient and/or partial occlusion of the pancreatic duct is achieved by the method according to the above-mentioned aspect/embodiments of the present disclosure.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

The present description will be better understood from the following detailed description read in light of the accompanying drawings, where.

In accordance with common practice, the various described features/elements are not drawn to scale but instead are drawn to best illustrate specific features/elements relevant to the present invention. Also, like reference numerals and designations in the various drawings are used to indicate like elements/parts.

DESCRIPTION

The patent or application file contains at least one drawing executed in color, Copies of this patent or patent application publication with color drawings) will be provided by the Office upon request and payment of the necessary fee. The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the entire application (including the specification, examples, and appended claims) are collected here. Unless otherwise defined herein, scientific and technical terminologies employed in the present disclosure shall have the meanings that are commonly understood and used by one of ordinary skill in the related art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/ working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "body fluid" herein is used in its broadest sense, referring to any fluid of a mammal, and is intended to include urine, stool, blood, spinal fluid, cerebrospinal fluid, ocular lens liquid, semen, synovial fluid, peritoneal fluid, pleural fluid, sputum, lymph fluid, saliva, amniotic fluid, sweat, bile, tears, gastric juice, pancreatic juice, breast milk, mucus, pericardial fluid, lymph, chyme, prostatic fluid. In particular, the term "body fluid" is referred to those that are delivered from a first tissue/organ to a second tissue/organ via a vessel or a duct. Illustrative examples of such vessels or ducts include, but are not limited to the blood vessel, lymphatic duct, cystic duct, common hepatic duct, common bile duct, pancreatic duct, and parotic duct.

The term "subject" as used herein includes human and veterinary subjects. "Mammal" for purposes of the present disclosure refers to any animal classified as a mammal, including human, domestic and farm animals, nonhuman primates, zoo, sports, or pet animals, such as dogs, horses, cats, cows, etc., and any other animal that has mammary tissue.

As used herein, the term "pancreatic duct" includes the accessory pancreatic duct, dorsal pancreatic duct, main pancreatic duct, and ventral pancreatic duct, as well as any branch from the pancreatic duct.

The term "partial occlusion," as used herein, denotes the state where the flow of the body fluid within a vessel or a duct is only partially occluded, e.g. 10% or more, which results in the temporary reduced flow velocity of the fluid flowing in the vessel or duct and an increased pressure of the vessel or duct. Partial occlusion of a vessel or duct may cause mild inflammation in the tissue or organ (including gland) associated with said vessel or duct. Indication relating to the extent of occlusion is obtained by measuring fluid pressure or fluid flow velocity, before, during, and after the application of the present method.

As used herein, the term "neogenesis" is intended to mean the regeneration or de novo growth of cells.

The terms "treatment" and "treating" are used herein to generally mean obtaining a desired pharmaceutical and/or physiological effect. Preferably, the effect is therapeutic in terms of partially or completely curing diabetes or other metabolic disorders associated with the malfunction of pancreas. Specifically, the term "treating" as used herein refers to application of the flow control device, system and/or method of the present disclosure to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable.

One aim of the present disclosure is to provide a reliable means for controlling the flow of a body fluid from a first tissue/organ to a second tissue/organ of a subject so as to transiently and/or partially occluding a vessel or duct for delivering the body fluid. Without being bound by theory, it is believed that the transient and/or partial occlusion of the vessel or duct may cause mild inflammation in the tissue/ organ associated with the vessel or duct. To this end, in the first aspect of the present disclosure, a flow control device for controlling the flow of a body fluid from a first organ to a second organ of a subject is provided. One exemplary device is illustrated in FIG. 1.

Figure 1:
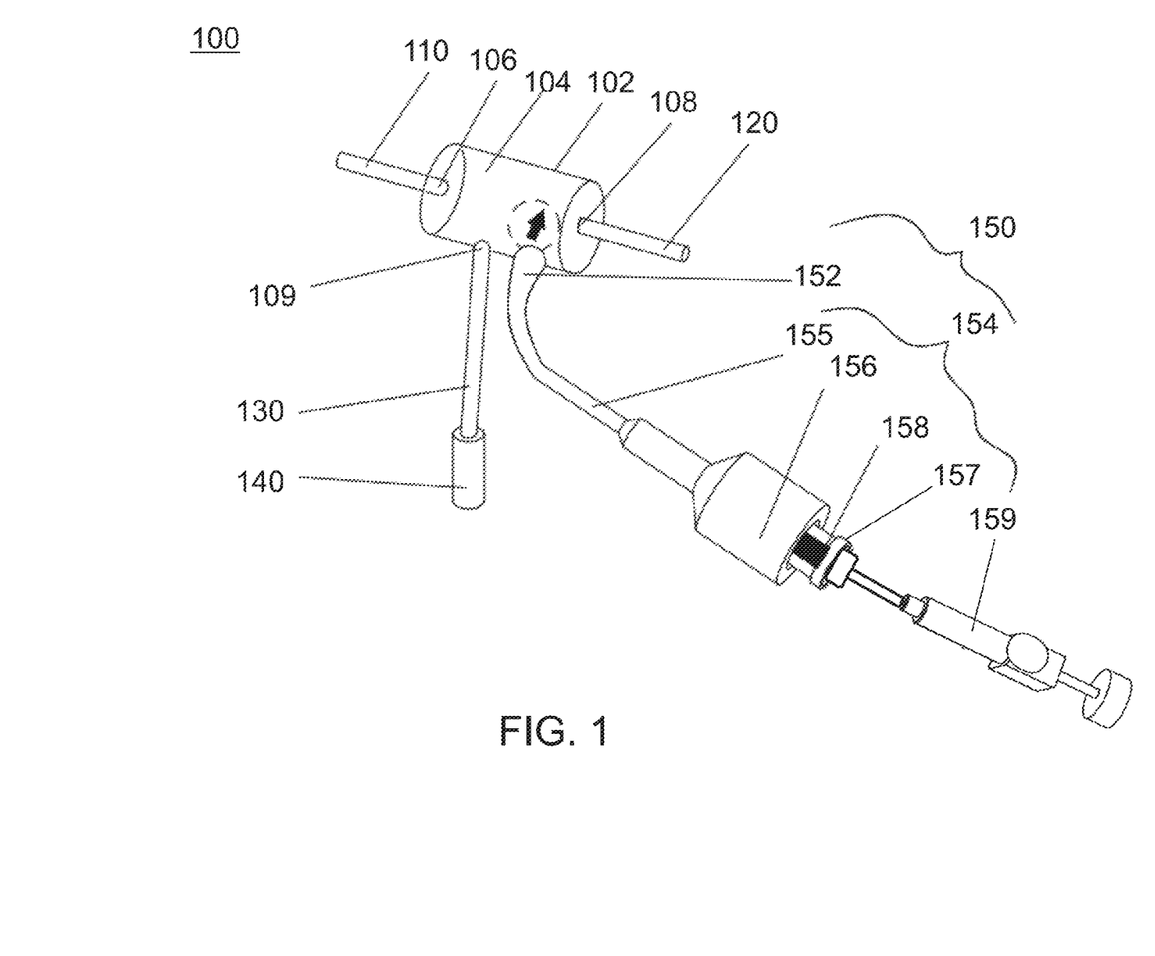
FIG. 1 is a schematic diagram illustrating a flow control device according to one embodiment of the present disclosure.

With reference to FIG. 1, the present invention provides a flow control device 100 that comprises a main body 102, a first fluid channel 110, a second fluid channel 120, a detection member 140, and a control member 150. As could be appreciated, the body fluid to be controlled by the present device 100 is not of particular limitation. In one example, the body fluid is the pancreatic juice flowing from the pancreas to the duodenum via the pancreatic duct. Other illustrative examples of body fluids include blood flowing within the vessel, and the bile flowing from the gallbladder to the duodenum via the common bile duct.

The main body 102 defines an interior lumen 104 for accommodating the body fluid flowing from the first tissue/ organ into the lumen via a vessel or duct. The main body 102 has a first opening (i.e., an inlet) 106 and a second opening (i.e., an outlet) 108. As illustrated in FIG. 1, the first opening 106 and second opening 108 are respectively disposed at the opposing ends along the longitudinal axis of the main body 102; however, the present invention are not limited thereto. Rather, the first opening 106 and an second opening 108 could be configured in any way such that the lumen 104 is capable of accommodating a fluid flowing from the vessel or duct (not shown) through the first opening 106 into the lumen 104 and allowing the fluid flowing out of the lumen 104 through the second opening 108 into the receiving organ or tissue (that is, the second tissue/organ), once the main body 102 is inserted into the subject at a desired position.

According to embodiments of the present disclosure, the lumen 104 may be in fluid communication with the vessel or duct. For example, the flow control device 100 may comprise an optional first fluid channel 110 to provide a fluid communication. The first fluid channel 110 has a proximal end and a distal end. The proximal end of the first fluid channel 110 is proximal to the main body 102, and for example, is connected to the first opening 106 of the main body 102; while the distal end of the first fluid channel 110 is distal to the main body 102 and operable to be connected to the vessel or duct when in use. Similarly, the lumen 104 may be in fluid communication with the receiving organ or tissue. According to certain embodiments, a second fluid channel 120 is used to provide such fluid communication. The second fluid channel 120 also has a proximal end and a distal end, in which the proximal end of the second fluid channel 120 is proximal to the main body 102, and for example, is connected to the second opening 108; while the distal end of the second fluid channel 120 is distal to the main body 102, and is operable to be connected to the receiving organ or tissue. In practice, the first and/or second fluid channel may be embodied with a medical tube including, among other things, catheters, stents or a combination of the two.

Figure 2:
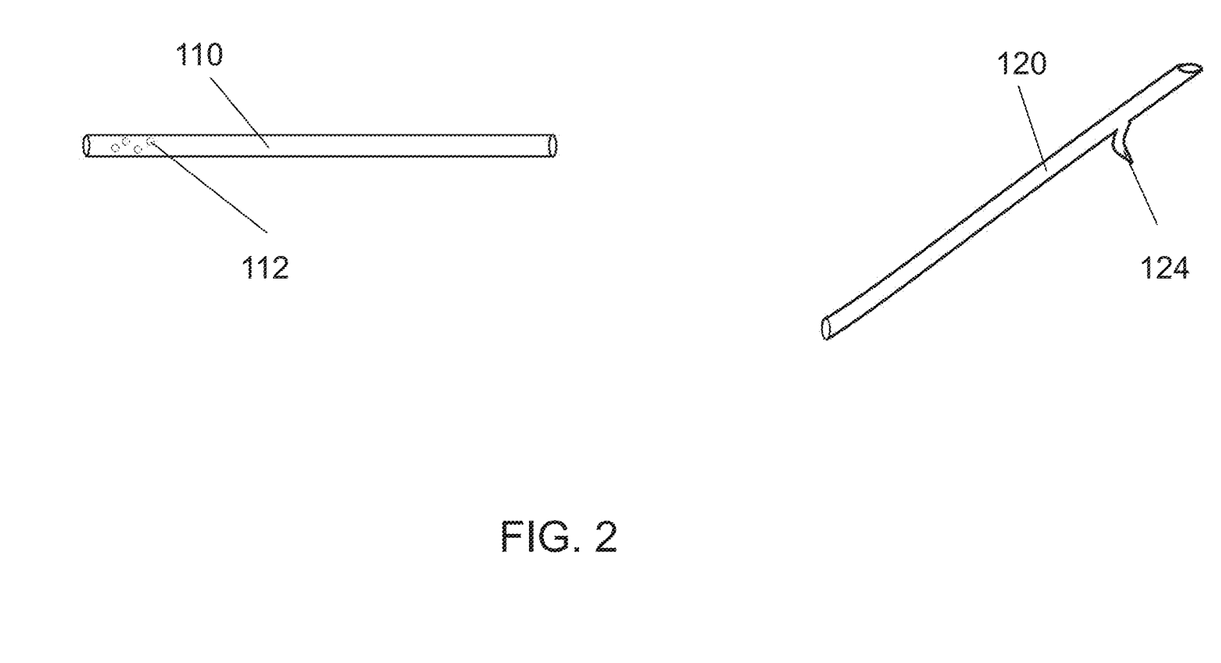
FIG. 2 is a schematic diagram illustrating a first fluid channel and a second fluid channel according to optional embodiment of the present disclosure.

Referring to FIG. 2, according to optional embodiments of the present disclosure, the first fluid channel 110 may have a plurality of first openings 112 disposed on the surface of at least a portion thereof. Similarly, in optional embodiments, the second fluid channel 120 may have a plurality of second openings (not shown) disposed on the surface of at least a portion thereof. These opening are disposed to facilitate the inflow or outflow of the body fluid to or from the main body 102.

Still optionally, the outer surface of the first fluid channel and/or the outer surface of the second fluid channel may have at least one flap extended therefrom. Preferably, the flaps can be disposed at the distal end of the first and/or second fluid channel for better retention of the first and/or second fluid channel within the vessel/duct and/or the tissue/organ. For example, the second fluid channel 120 illustrated in FIG. 2 has one flap 124 extended from the outer surface of the second fluid channel 120.

In another optional embodiment, the diameter of the distal end of the first fluid channel 110 is less than the diameter of the distal end of the second fluid channel 120. It should be noted that two or more of the above-mentioned optional features regarding the first or second fluid channel could be combined in a single embodiment.

As could be appreciated, the fluid communication between the lumen 104 and the vessel/duct or receiving tissue/organ can be direct or indirect fluid communication. For example, when the length of the first fluid channel 110 or the second fluid channel 120 is relatively long, the fluid communication is considered an indirect fluid communication. Alternatively, the control device may further comprise other tube or means connecting the first fluid channel 110 or the second fluid channel 120 and the vessel/duct or receiving tissue/organ; in this case, the fluid communication is also considered indirect. On the other hand, in the event where the length of the first fluid channel 110 or the second fluid channel 120 is relatively short or even negligible, the fluid communication between the lumen 104 and the vessel/duct or receiving tissue/organ could be considered a direct fluid communication. It should be noted that, throughout the present disclosure, the above discussion regarding the direct or indirect fluid communication is applicable to the fluid communication between or among two or more elements, element(s) and workpiece(s) (e.g., vessel, duct, tissue or organ), workpieces, etc.

Returning back to FIG. 1, the flow control device 100 also comprises a detection member 140. The detection member 140 is in fluid communication with the lumen 104. As exemplified in FIG. 1, an optional third fluid channel 130 connecting the detection member 140 and a third opening 109 of the main body 102 is used to establish the fluid communication between the detection member 140 and the lumen 104. In alternative embodiments, the detection member (not shown) may be disposed within the lumen 104, thereby forming a direct fluid communication with the lumen 104. The detection member 140 is operable to detect at least one of the following parameters: flow rate, velocity, flow resistance and pressure of the body fluid.

The detection member 140 could be embodied in any of the known devices and techniques suitable in the detection of any of the above-mentioned parameters. For example, the detection member 140 may optionally comprise a pressure sensor (not shown) for detecting the pressure that the body fluid places on the wall of the vessel or duct.

Additionally or alternatively, the detection member 140 may optionally comprise a sampling unit (not shown) that is operable to withdraw a fluid sample from the lumen 104 for further analysis.

The flow control device 100 also comprises a control member 150. The control member 150 is operable to control the flow rate, velocity, flow resistance, or pressure of the fluid from the lumen 104 through the second opening 108 based on the at least one detected parameter described above, such that the flow of the body fluid from the first tissue/organ to the second tissue/organ via the vessel or duct is transiently and/or partially occluded.

One exemplified control member 150, as illustrated in FIG. 1, comprises an inflatable balloon 152 and an inflator 154. The inflatable balloon 152 is disposed within the main body 102, and the inflator 154 is in fluid communication with the inflatable balloon 152. According to one optional embodiment, the inflator 154 has a tube 155 having a proximal end connected to the inflatable balloon 152. The inflatable balloon 152 as illustrated by solid line in FIG. 1 is in the un-inflated state; yet it is and operable to be inflated (illustrated by dash line in FIG. 1) by the inflator 154 so as to partially occlude the flow of the fluid from the lumen 104 through the second opening 108 to the receiving tissue or organ. In one embodiment, the inflator 154 comprises an air pump 159 that may supply air through the tube 155 to the inflatable balloon 152 for selectively inflating the inflatable balloon 152. More specifically, the inflator 154 comprises a coupling member 157 for connecting the tube 155 and the air pump. The coupling member 157 is connected to a distal end of the tube 155, and is held in place by an elastic sleeve 156 fitted around the tube 155 and the coupling member 157. Disposed within the coupling member 157 is a plug 158 which is compressible under the action of the pressure provided by the air pump 159, thereby allowing for the selective inflation of the inflatable balloon 152, as well as the maintenance of the inflated state of the inflatable balloon 152.

Figure 3:
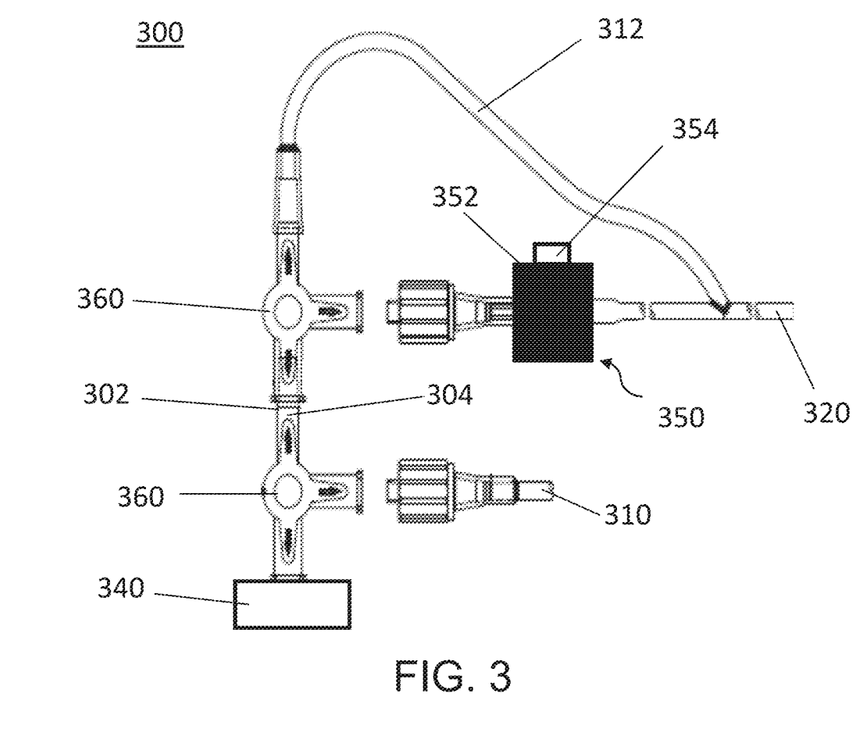
FIG. 3 is a schematic diagram illustrating a flow control device according to another embodiment of the present disclosure.

Another embodiment of the flow control device 300 according to the present disclosure is illustrated in FIG. 3.

As illustrated, the flow control device 300 comprise a main body 302 that defines a lumen 304; a first fluid channel 310 operable to be in fluid communication with the lumen 304 and the first tissue/organ of the subject (not shown); a second fluid channel 320 operable to be in fluid communication with the lumen 304 and the second tissue/organ of the subject (not shown); a detection member 340 operable to be in fluid communication with the lumen 304 for detecting at least one parameter selected from the group consisting of the flow rate, velocity, flow resistance and pressure of the body fluid; and a control member 350 operable to control the flow of the body fluid from the first tissue/organ to the second tissue/organ of the subject.

The control member 350 comprises a pump 352 disposed between the second fluid 320 channel and the main body 302; however, the present invention is not limited thereto; rather, in other embodiments, the pump 352 could be disposed between the first fluid 310 channel and the main body 302. The pump 352 is operable to provide an output pressure for controlling the flow of the body fluid into and/or from the lumen 304.

In certain optional embodiments, the control member 350 further comprises an adjustment member 354 operatively connected to the pump 352 for adjusting the magnitude of the output pressure of the pump 352.

Still optionally, the flow control device 300 may further comprises a side fluid channel 312 branching from the first fluid channel 310 and operable to be in fluid communication with the first fluid channel 310 and the lumen 304. The fluid communication between the first fluid channel 310 and the lumen 304 via the side fluid channel 312 allows the body fluid to flow into the lumen without passing through the pump 352, therefore, in some circumstances, the flow of the body fluid may be maintained (or partially maintained) even when the pump 352 is switched off.

According to optional embodiments of the present disclosure, the control member 350 comprises at least one pressure valve (not shown) operable to control the flow of the body fluid into and/or from the lumen. For example, the pressure valve could be disposed between the first fluid channel 310 and the lumen 304 so as to control the inflow of the body fluid from the first fluid channel 320 to the lumen 304.

Alternatively or additionally, the pressure valve could be disposed between the second fluid channel 320 and the lumen 304 so as to control the outflow of the body fluid from the lumen 304 to the second fluid channel 320. Similarly, the pressure valve could be alternatively or additionally disposed between the lumen 704 and the detection member 340 so as to control the outflow of the body fluid from the lumen 304 to the detection member 340.

In some optional embodiments, the control member 350 may comprise at least one freeze valve (not shown). Structure of the Freeze valve is known in the art. For example, U.S. Pat. No. 6,311,713 disclosed various embodiments of freeze valves and method of controlling liquid flow using the freeze valve. The entirety of U.S. Pat. No. 6,311,713, in particular the structures illustrated in the drawings and accompanying descriptions, is incorporated herein by reference.

According to certain optional embodiments of the present disclosure, the flow control device 300 may comprise at least one multi-way valve 360 that comprises at least two nozzles. For example, the two multi-way valves 360 illustrated in FIG. 3 are both three-way valves respectively having three nozzles.

Depending on the actual arrangement, the multi-way valve is operable to establish the fluid communication between any two of the lumen 304, the first fluid channel 310, the second fluid channel 320 and the detection member 330.

Figure 4:
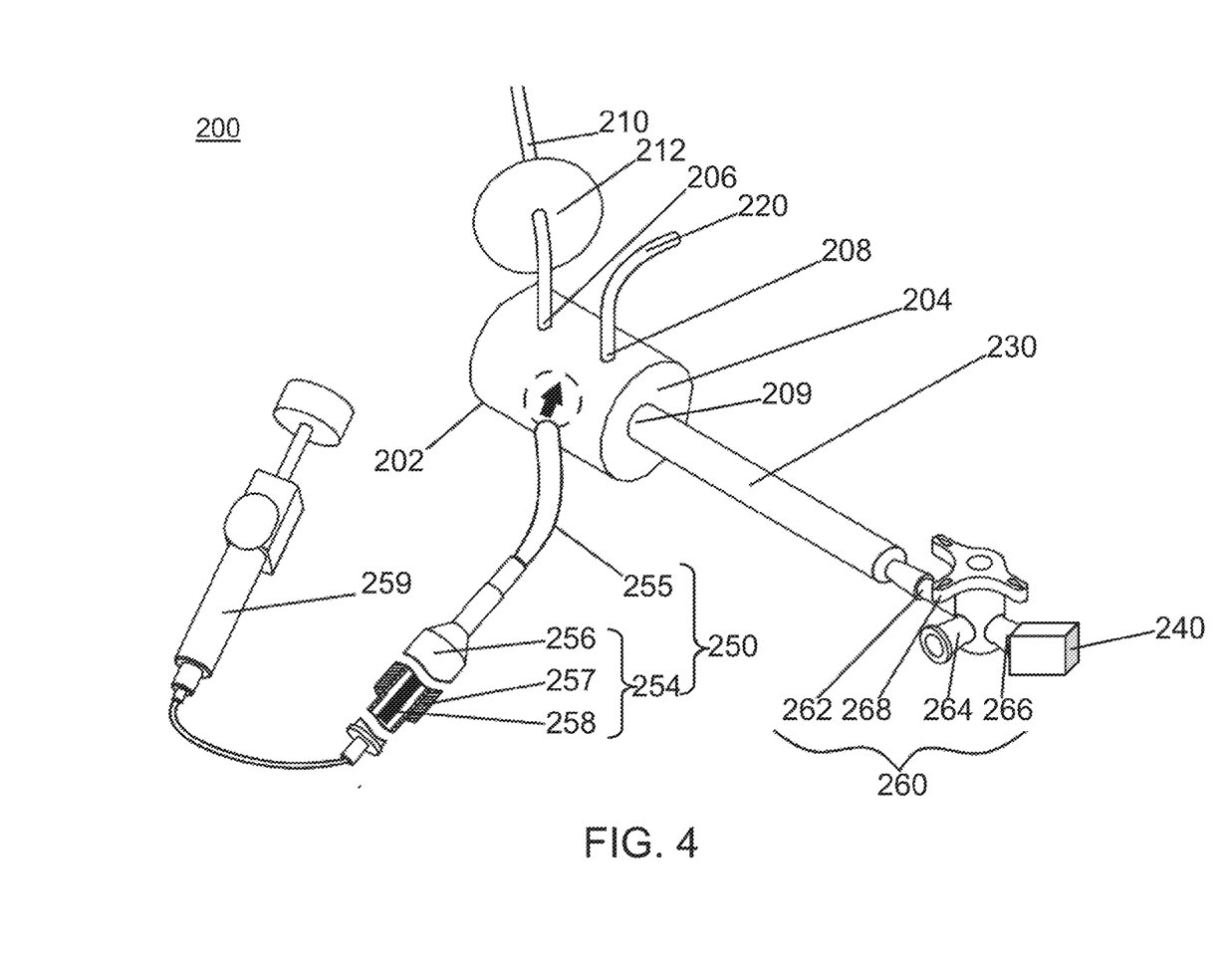
FIG. 4 is a schematic diagram illustrating yet another flow control device according to another embodiment of the present disclosure.
Figure 5:
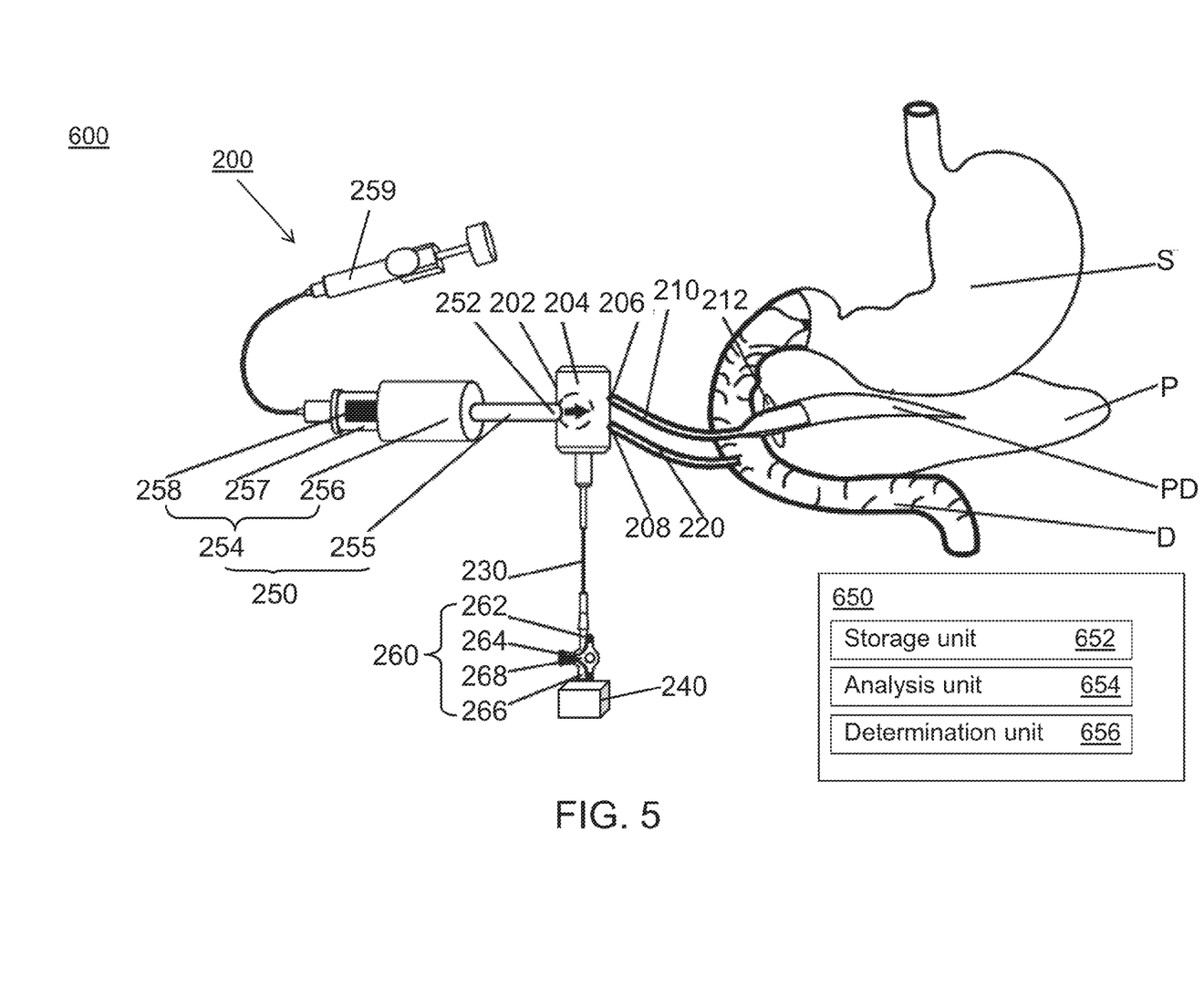
FIG. 5 is a schematic diagram illustrating a flow control system comprising the flow control device of FIG. 4 as used in a subject according to one embodiment of the present disclosure.

FIG. 4 depicts another flow control device 200 for controlling the flow of a body fluid from a first tissue/organ to a second tissue/organ of a subject according to another embodiment of the present disclosure, and FIG. 5 schematically illustrates a flow control system 600, which comprises the flow device 200 and computing device 650, as used in a subject for inducing mild inflammation or microinjury in a first and/or second tissue/organ of a subject by controlling the flow of a body fluid from the first tissue/organ to the second tissue/organ of the subject according to one embodiment of the present disclosure. For the purpose of illustration, the following discussion is directed to the control of pancreatic juice; however, as could be appreciated, the scope of the present invention is not limited thereto.

Similar to the flow control device 100 of the above embodiment, the flow control device 200 of FIG. 4 comprises a main body 202, three fluid channels 210, 220, and 230, a detection member 240, and a control member 250. The flow control system 600 of FIG. 5 comprises the flow control device 200 and a computing device 650 in which the computing device 650 is in operative connection with the flow control device 200, and is configured to allow the control member 250 to control the flow of the body fluid from the first tissue/organ to the second tissue/organ of the subject based on a detection result obtained by the detection member 240. To do so, the computing device 650 may optionally comprise at least one of the following units, the storage unit 652, the analysis unit 654, and the determination unit 656.

The computing device 650 could be implemented as personal computers, server computers, hand-held or laptop devices, personal digital assistants, smart phones, multiprocessor device systems, microprocessor device-based systems, programmable consumer electronics, network PCs, minicomputers, mainframe computers, distributed computing environments that include any of the above systems or devices, and the like. The computing device 650 may be described in the general context of computer-executable instructions, such as program modules, executed by one or more computers or other devices. Generally, program modules include routines, programs, objects, components, data structures, and/or other elements that perform particular tasks or implement particular abstract data types. Typically, the functionality of the program modules may be combined or distributed as desired in various implementations.

The storage unit 652 is configured to store a set of data of the relationship between an injury level of the first tissue/organ and at least one parameter selected from the group consisting of the flow rate, velocity, flow resistance and pressure of the body fluid so that the control member 250 is operable to control the flow of the body fluid from the first tissue/organ to the second tissue/organ of the subject based on the detection result obtained by the detection member 240 and the set of data stored in the storage unit 652.

In implementation, the storage unit 652 includes volatile, nonvolatile, removable, and non-removable media implemented in any method or technology for storage of information. Examples of storage unit 652 suitable for use herein include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by the flow control system 600.

The analysis unit 654 is configured to analyze the detection result obtained by the detection member 240, such that the control member 250 is operable to control the flow of the body fluid from the first tissue/organ to the second tissue/organ of the subject based on the analysis result obtained by the analysis member 654.

The determination unit 656 is configured to make a determination based on the detection result obtained by the detection member 240, and the control member 250 is operable to control the flow of the body fluid from the first tissue/organ to the second tissue/organ of the subject based on the determination result obtained by the determination unit 656.

The analysis unit 654 and the determination unit 656 could be respectively implemented as software, hardware, firmware, or a combination thereof depending on the actual need of the implementer.

Still optionally, the flow control system 600 may comprise a wireless communication module (not shown) for establishing a communication connection between the flow control device 200 and the computing device 650. Alternatively, the flow control device 200 and the computing device 650 could communicate in a wired manner, e.g., they could be connected with a cable or wire. Still alternatively, there is only functional connection between the flow control device 200 and the computing device 650, they are not communicatively connected via wireless or wired connections. For example, the data or instructions from the computing device 650 could be stored in a removable storage medium (such as a USB memory stick or a compact disk), and the flow control device 200 may have a processing unit for accessing the data or instructions in the removable storage medium.

Still referring to FIG. 5, the first fluid channel 210 is arranged to establish the fluid communication between the lumen 204 and the main pancreatic duct (PD) of the subject; while the second fluid channel 220 is arranged to establish the fluid communication between the lumen 204 and the duodenum (D) of the subject. In particular, the proximal end of the first fluid channel 210 is connected to the first opening 206 of the main body 202, and the distal end of the first fluid channel 210 is arranged to locate in adjacent to the exit of the main pancreatic duct (PD). In this way, the pancreatic juice from the main pancreatic duct (PD) would flow into the lumen 204 via the first fluid channel 210. Optionally, a tab 212 is fixed to the outer surface of the first fluid channel 210 for holding the first fluid channel 210 in place. For example, the tab 212 may be stitched to the pancreas (P) with a surgical suture. Also, the proximal end of the second fluid channel 220 is connected to the second opening 208 of the main body 202, and the distal end of the second fluid channel 220 is arranged to form fluid communication with the duodenum (D) of the subject so that the pancreatic juice in the lumen 204 would flow into the duodenum (D) via the second fluid channel 220. Similarly and optionally, another tab (now shown) may be used to hold the second fluid channel 220 in place.

Referring to both FIG. 4 and FIG. 5, a third fluid channel 230 connecting a third opening 209 of the main body 202 and the detection member 240 is provided to establish the fluid communication between the lumen 204 and the detection member 240. In this particular example, the flow control device 200 further comprises an optional three-way valve 260. The three-way valve 260 has a first nozzle 262, a second nozzle 264, and a third nozzle 266. One of the three nozzles (e.g., the first nozzle 262) is connected to the distal end of the third fluid channel 230, while another nozzle (e.g., the third nozzle 266) is connected to the detection member 240. The three-way valve 260 also has a three-way stopcock 268, which is used to control the flow of the fluid (in this case, the pancreatic juice), so as to establish or interrupt the fluid communication between the lumen 204 and the detection member 240 as desired. Still optionally, the flow control device 200 may further comprise a sampling means (not shown) coupled to the second nozzle 264. The sampling means is operable to withdraw a fluid sample from the lumen 204 for further analysis. According to one embodiment of the present disclosure, the detection member 240, the three-way valve 260, and a portion of the third fluid channel 230 are arranged to be disposed outside the subject's body. For example, a surgical tape or cosmetic tape is used to tape the third fluid channel 230 and/or the three-way valve 260 to the subject's skin so as to hold the third fluid channel 230 and/or the three-way valve 260 in place.

Similar to the control member 150 of the flow control device 100, the control member 250 is operable to control the flow rate, velocity, flow resistance, or pressure of the fluid from the lumen 204 through the second opening 208 based on the at least one detected parameter described above, so as to transiently and partially occlude the main pancreatic duct (PD).

According to one embodiment of the present disclosure, an inflatable balloon 252 is disposed within the main body 202, whereas an inflator 254 is outside of the subjects' body and in fluid communication with the inflatable balloon 252 by means of a tube 255. A medical balloon pump 259 for selectively inflating the inflatable balloon 252 is depicted in FIG. 4 and FIG. 5; however, this medical balloon pump 259 is only provided for the purpose of illustration and is not intended as a limitation to the present disclosure. This medical balloon pump 259 allows the user (e.g., the subject or a medical practitioner) to operate with one hand thereby facilitating the control of the fluidic flow in the main pancreatic duct (PD).

Figure 6:
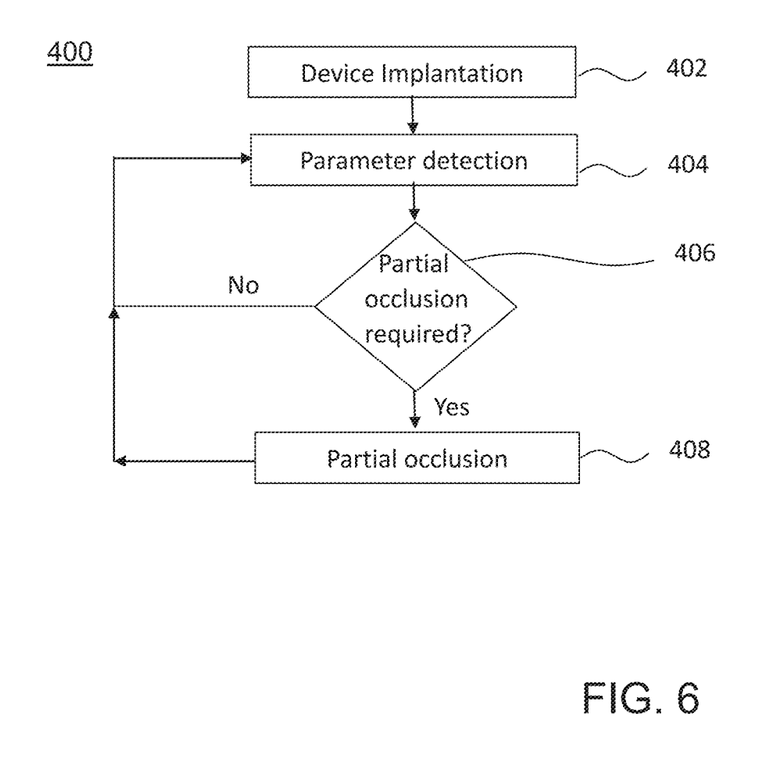
FIG. 6 is a flowchart of the method for inducing mild inflammation or microinjury in a subject according to some embodiments of the present disclosure.
Figure 7:
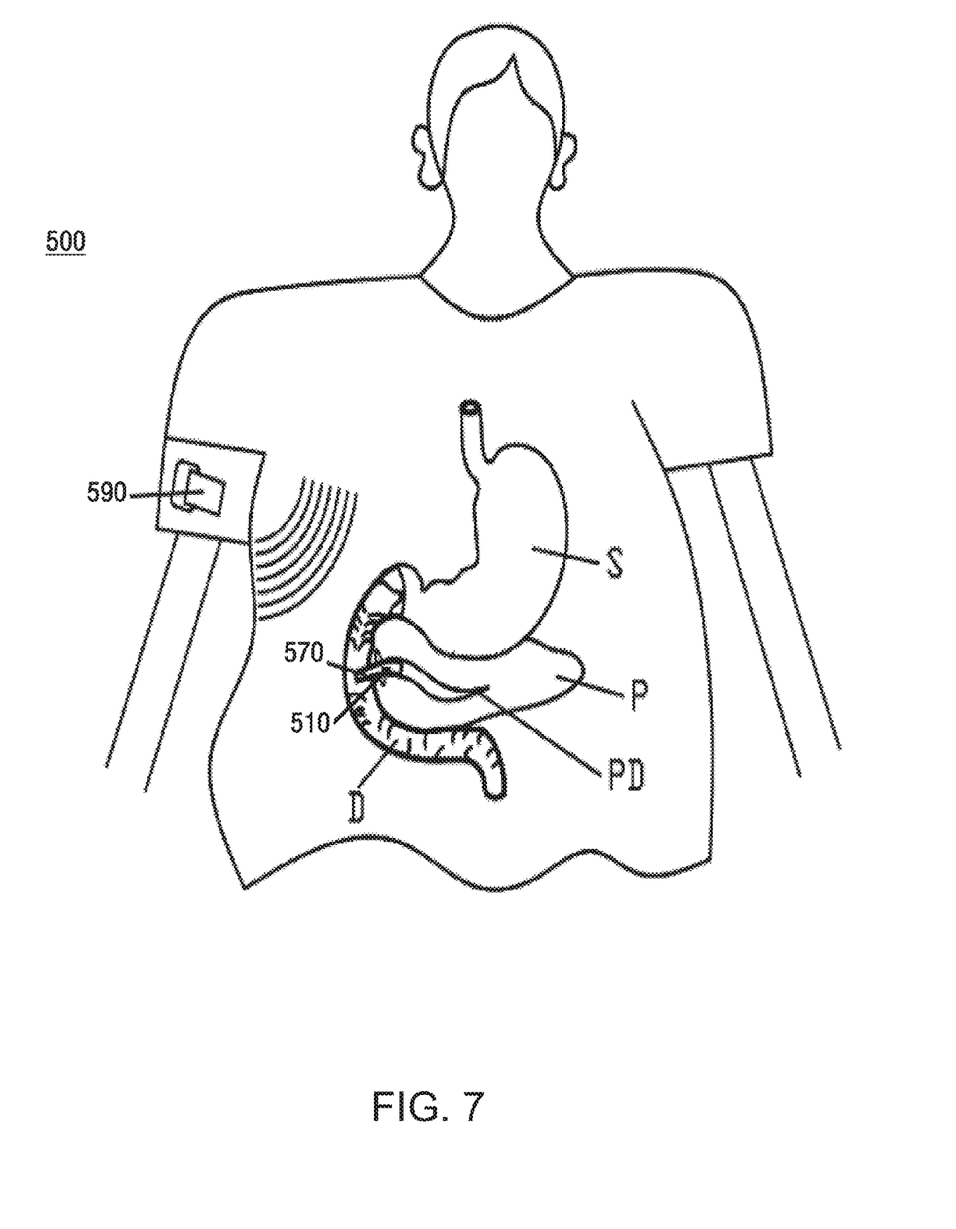
FIG. 7 is a schematic diagram illustrating a miniaturized flow control device as used in a subject to transiently and partially occlude the main pancreatic duct of the subject according to one embodiment of the present disclosure.

FIG. 6 is a flowchart illustrating the method 400 for inducing mild inflammation or microinjury in a first and/or second tissue/organ of a subject by controlling the flow of a body fluid from the first tissue/organ to the second tissue/organ of the subject according to some embodiments of the present disclosure.

In one embodiment, the method is used to control the flow of pancreatic juice from the pancreas to the duodenum via the pancreatic duct. Without being bound by theory, it is believed that the transient and/or partial occlusion of the main pancreatic duct may cause mild pancreatitis or pancreatic microinjury, which in turn may activate the self-repair mechanism of the pancreas that leads to neogenesis of exocrine pancreatic tissues (including acinar cells, centroacinar cells, and ducts) and/or endocrine pancreatic tissues (e.g., islets of Langerhans, including alpha cells, beta cells, delta cells, PP cells, and epsilon cells). Such neogenesis is advantageous in restoring the pancreatic function, and is believed to have broad prospect in treating disorders associated with pancreas malfunction, such as diabetes. Therefore, the present device and method are suitable for use in subjects having such disorders.

For the purpose of illustration, the method 400 is now explained with the flow control device 200 and flow control system 600 depicted in FIG. 5. However, the present method is not intended to be tied to this particular device; rather, any flow control devices falling in the scope of the present invention are equally applicable.

In step 402, the flow control device is arranged such that the distal end of the first fluid channel is adjacent to the exit of the first tissue/organ, thereby allowing the flow of the body fluid from the first tissue/organ into the lumen via the first fluid channel; and the distal end of the second fluid channel is connected to an opening of the second tissue/organ, thereby allowing the flow of the body fluid from the lumen into the second tissue/organ (duodenum) via the second fluid channel.

For example, the flow control device 200 is implanted as described above in connection with FIG. 5. Specifically, the main body 202, the first fluid channel 210, the second fluid channel 220, and a portion of the third fluid channel 230 and the tube 255 are implanted within the subject's body such that the distal end of the first fluid channel 210 is adjacent to the exit of the main pancreatic duct (PD) and the second fluid channel 220 is connected to the duodenum (D).

Next, in step 404, the detection member is used to detect at least one parameter selected from the group consisting of: the flow rate, velocity, flow resistance and pressure of the body fluid. For instance, the detection member 240 of FIG. 5 is used to detect the flow rate, velocity, flow resistance and/or pressure of the pancreatic juice. In one example, the detection member 240 is used to measure the pressure of the pancreatic juice places on the wall of main pancreatic duct (PD).

Then, in step 406, a determination is made as to whether the subject is in need of partial occlusion of the vessel or duct (e.g., the main pancreatic duct) and the extent of the occlusion. This determination could be made based on the result obtained in step 404. For example, in the case the pancreatic pressure is monitored, a pancreatic pressure suitable to induce mild inflammation or microinjury in the pancreas of a pig or human is about 10-50 $cmH_2O$. Accordingly, when the pancreatic pressure detected in step 404 is lowered or higher than the specified range, and in step 406, it is determined that a partial occlusion is required, then the method step proceeds to step 408.

Alternatively or additionally, the method 400 may further comprise a sampling step (not shown) to collect at least one body fluid from the subject. In certain embodiments, the pancreatic juice and/or blood could be collected, and the level of pancreatic lipase, pancreatic amylase, glucose, insulin or C-peptide of the subject could be detected. As could be appreciated, the insulin or the blood glucose level may be directly measured using suitable sensors, such as using fiber optic sensors or limited use chemical assay sensors; and hence, in this cases, the detection could be conducted in situ, and there is no need to separate the blood sample from the body. In the case where this addition detection is conducted, the determination step 406 could be made further based on the detected level of pancreatic lipase, pancreatic amylase, glucose, insulin or C-peptide of the subject. For example, if the insulin level is too low or the blood glucose level is too high, the subject is determined to subject to the partial occlusion of the main pancreatic duct (PD) as described in step 408.

On the other hand, if the detected parameter(s) indicate that the partial occlusion is not required, the subject's physiological parameters are continually monitored and evaluated in a periodic basis (steps 404 and 406).

In the partial occlusion step 408, the inflatable balloon 252 is inflated to partially occluding the main pancreatic duct (PD) in which the extent of the partial occlusion is sufficient to cause mild pancreatitis or pancreatic microinjury in the subject's pancreas. For example, for a pig or human, the main pancreatic duct is partially occluded to result in a pancreatic pressure of about 10-50 $cmH_2O$; preferably, 20-35 $cmH_2O$. For example, the pancreatic pressure may be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 $cmH_2O$. In one example, the subject or a medical practitioner may use the medical balloon pump 259 to selectively inflate/deflate the inflatable balloon 252 and control the inflated level of the inflatable balloon 252 such that the pancreatic pressure of the subject is maintained in the range of 10-50 $cmH_2O$, or preferably, 20-35 $cmH_2O$.

Then, the control member is used to control the flow of the body fluid by adjusting at least one of the flow rate, velocity, flow resistance and pressure of the body fluid to an extent sufficient to cause the mild inflammation or microinjury of the first and/or second tissue/organ of the subject.

For example, the control member 250 comprises an inflator 250 that is configured to control the inflation and/or deflation of the inflatable balloon 252. In this way, the flow of the pancreatic juice to or from the lumen 204 can be controlled by adjusting the inflation state of the inflatable balloon 252.

During the course of the partial occlusion, the subject's physiological parameters are monitored and evaluated continuously in steps 404 and 406. For example, the pancreatic pressure is detected (step 404), the insulin, blood glucoses level and/or inflammatory marker(s) are detected (sampling step, not shown), and the detected parameters are used to evaluate whether the treatment is effective in restoring the pancreatic function (step 406), and to evaluate the inflammatory or the microinjury level of the pancreas (step 406). The evaluation result is used to determine whether the partial occlusion or an adjustment to the partial occlusion level is required (step 406). If the evaluation indicates that the status quo shall be maintained, then monitoring and evaluating the subject's physiological parameters in a periodic basis by repeating steps 404 to 408, such as every 20 min. On the other hand, if the evaluation indicates that the partial occlusion level shall be adjusted, the method stops.

During the partial occlusion step 408, the subject or the medical practitioner may use the medical balloon pump 259 to increase or reduce the volume of the inflatable balloon 252 so as to increase or reduce the occlusion level of the main pancreatic duct (PD). For example, if the pancreatic pressure is too high (e.g., higher than 50 $cmH_2O$), the volume of the inflatable balloon 252 shall be reduced so as to increase the flow from the main pancreatic duct (PD) to the duodenum (D), thereby reducing the pancreatic pressure to avoid the risk of acute pancreatitis. In another example, when the pancreatic pressure is too low (e.g., lower than 10 $cmH_2O$) and the insulin level is still under normal level, the volume of the inflatable balloon 252 could be increased so as to further decrease the flow from the main pancreatic duct (PD) to the duodenum (D), thereby increasing the pancreatic pressure to induce the neogenesis of the pancreatic tissue (in particular, the islet neogenesis). Physical activities may also affect the flow of body fluids. For example, the increased secretion of the pancreatic juice after meal would lead to higher pancreatic pressure, and hence, the volume of the inflatable balloon 252 could be reduce so as to facilitate the drainage of the pancreatic juice after meal.

In an optional embodiment, the computing device 650 of FIG. 5 comprises the storage unit 652, the analysis unit 654 and the determination 656, and the flow control system implements the method 400 as follows. In step 402, the flow control device 200 is arranged as discussed hereinabove with respect to FIG. 4 and FIG. 5 so as to allow the flow of the body fluid (e.g., pancreatic juice in this case) into the flow control system 200. Then, in step 404, the detection member 240 detects at least one parameter selected from the group consisting of the flow rate, velocity, flow resistance and pressure of the body fluid. Next, the analysis unit 654 analyze the detection result obtained by the detection member 240 based on the data stored in the storage unit 652. Specifically, the data stored in the storage unit 652 dictates the injury level of the first tissue/organ and the at least one parameter associated with the body fluid. Then, the determination unit 656 makes a determination based on the analysis result obtained by the analysis unit 654. The determination result from the determination unit 656 is then communicated to the control member 250 (e.g., by wireless communication) such that the control member 250 controls the flow of the body fluid from the first tissue/organ to the second tissue/organ of the subject based on the determination result.

One embodiment of the present disclosure is a miniaturized device for transiently and partially occluding an exocrine duct. One exemplary miniaturized device 500, as used to transiently and partially occluding the main pancreatic duct, is depicted in FIG. 3.

The miniaturized device 500 comprises a main body 570 for being implanted into a subject's body; and a transceiver 590 for being placed outside of the subject's body. Similar to the flow control device 100 illustrated in FIG. 1, the main body 570 also defines a lumen and has a first opening (i.e., an inlet) and a second opening (i.e., an outlet). The lumen is operable to accommodate the pancreatic juice flow from the main pancreatic duct through the first opening into the lumen. The miniaturized device 500 also comprises at least one sensor for detecting at least one of the following parameters: the flow rate, velocity, flow resistance and pressure of the pancreatic juice, the level of the pancreatic lipase or amylase in the pancreatic juice, and the blood level of glucose, insulin, or C-peptide. For example, at least one thin-film transistor sensor 510 may be disposed on the inner wall of the main body 570, such that the thin-film transistor sensor 510 is in contact with the pancreatic juice within the lumen. The miniaturized device 500 may optionally comprise at least one transmitter (not shown) for wirelessly transmitting the detected parameter(s) to the transceiver 590. The transceiver 590 is also operable to receive a command that dictates the desired flow parameter(s) associated with the pancreatic juice (e.g., the flow rate, velocity, flow resistance, or pressure of the pancreatic juice). The miniaturized device 500 may also comprise a control member (not shown) and a receiver (not shown), in which the receiver is operable to wirelessly receive the command transmitted from the transceiver 590, and the control member (e.g., a micro-pump which is powered by radio frequency) is operable to control the flow rate, velocity, flow resistance, or pressure of the pancreatic juice from the lumen through the second opening according to the command.

The main body 570 may be implanted to a site adjacent to the exit of the main pancreatic duct by an endoscopic surgery. Generally, the first opening of the main body 570 may be about 0.8-5 mm in diameter, the second opening of the main body 570 may be about 0.8-10 mm in diameter, and the length of the main body 570 in the longitudinal direction is about 10 mm.

According to the principles and spirit of the present disclosure, the flow control device and/or method for transiently and partially occluding the exocrine duct have broad prospect in the medical field. For example, the flow control device may cause partial occlusion in the pancreatic duct (in particular, main pancreatic duct) which may lead to islet neogenesis in the subject, and thereby restore the insulin secretion function in the subject. Accordingly, the present device and method are suitable for treating patients having diabetes mellitus without the need of the administration of exogenous insulin.

The present flow control devices could be made of biocompatible materials that would not induce rejections by the body. In addition, once the subject retains normal or desired blood glucose control ability, the present device could be removed from the subject's body. That is, the present flow control devices and methods would not result in irreversible damages to the subject in the course of the treatment.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example I

Lanyu pigs (3-5 weeks old; male; 16-22 kg) purchased from Taitung Animal Propagation Station (Taiwan) were used in the present working example to investigate the induction of mild inflammation or microinjury in the pancreas by the flow control device according to embodiments of the present disclosure. The flow control device used in this example was similar to the flow control device 300 of FIG. 3. This experiment was approved by the Mackay Memorial Hospital Review Board (New Taipei City, Taiwan, R.O.C.) and was performed in compliance with national animal welfare regulations. Animals were allowed free access to water and quota diet and were monitored regularly during the experimentation.

The pig was fasted for 12 hours, before the induction of anesthesia using Zoletil at a dosage of 4-8 mg/kg given intramuscularly, followed by air anesthesia with 2% Isoflurane. After sterilization with the iodine solution and ethanol, the abdominal cavity was open. The ampulla of Vater located around the first 4 to 5 cm of the duodenum was found, and the first 2 to 2.5 cm of the distal end of the first fluid channel 310 was inserted into the main pancreatic duct, then the tab (not shown in FIG. 3) fixed on the first fluid channel 310 was stitched to the intestinal wall in adjacent to the ampulla of Vater to prevent the first fluid channel 310 from falling out of the main pancreatic duct. The distal end of the second fluid channel 320 was inserted into the duodenum, and the tab (not shown in FIG. 3) on the second fluid channel 320 was stitched to the duodenum wall. The remaining portions of the first and second fluid channels 310 and 320, together with main body 302 were disposed outside the pig's body before the duodenum and the abdominal cavity were closed. The whole procedure was performed under sterile surgical Conditions. After the closure, the pump 352 was attached to the main body 302 and then turned on, so that the pancreatic juice was withdrawal from the pancreas under the suction force of the pump 352.

Four days after the surgery, the pig was sacrificed and pancreatic tissue was harvested. The samples were fixed in 10% neutral formalin and embedded in paraffin blocks to obtain longitudinal section. Before use, fixed samples were de-paraffinized in xylene and rehydrated in a graded series of ethanol. General histology was performed using H&E dye. Digital photomicrographs (Zeiss epifluorescence microscope; Jena, Germany) were taken from representative areas at a fixed magnification of 100×.

Figure 8:
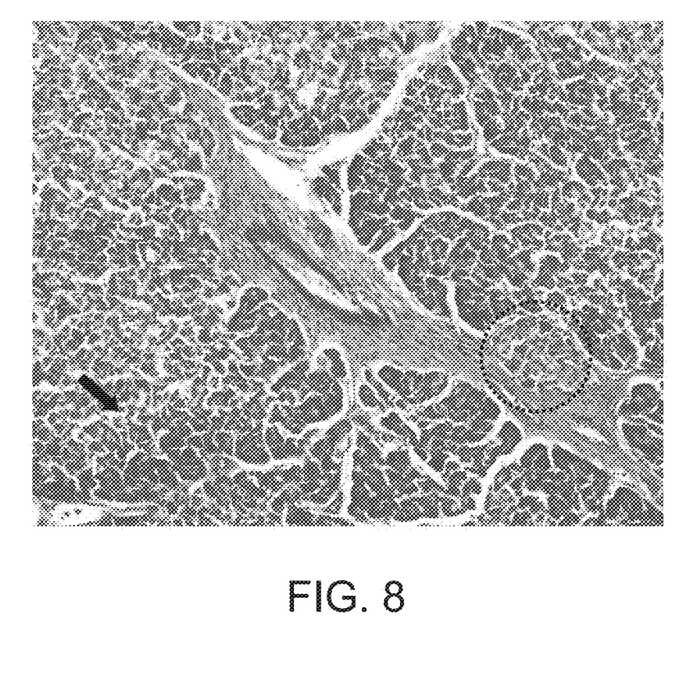
FIG. 8 is a representative photographs illustrating the histology of the pancreas of the pig treated with the flow control device according to one embodiment of the present disclosure.

FIG. 8 is a representative photograph of the pancreas sections. The histological analysis indicated that the installment of the flow control device did not cause acute pancreatitis, and there were less than five neutrophils observed at 100× magnification (see, the solid arrow in FIG. 8). Also, for cells adjacent to the main pancreatic duct (less than 3.5 mm from the main pancreatic duct), about 60% of the exocrine cells were damaged, while the endocrine cells were substantially free from damage (see, the dotted circle in FIG. 8). Meanwhile, less damage was observed in cells distal to the main pancreatic duct, as compared to the exocrine cells adjacent to the main pancreatic duct (see, the dotted circle in FIG. 8).

The results indicate that the present flow control device could induce mild inflammation or microinjury in the pancreas of a subject by controlling the flow of the pancreatic juice from the pancreas to the duodenum of the subject. Further, the application of the present flow control device would not result in acute inflammation or severe injury to the associated tissues/organs. Therefore, the present flow control device and flow control system are useful in establishing animal models with mild inflammation or microinjury in a desired organ by using the method provided herein.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A flow control device for controlling the flow of a body fluid from a first tissue/organ to a second tissue/organ of a subject, comprising,
   a main body that defines a lumen, wherein a housing of the main body comprises a first opening and a second opening separated from the first opening;

a first fluid channel, connected to the main body via the first opening, and operable to be in fluid communication with the lumen and the first tissue/organ of the subject;

a second fluid channel, connected to the main body via the second opening, and operable to be in fluid communication with the lumen and the second tissue/organ of the subject, wherein the first and second fluid channels respectively comprise a proximal end proximal to the main body and a distal end distal to the main body;

a detection member, operable to be in fluid communication with the lumen for detecting at least one parameter selected from the group consisting of the flow rate, velocity, flow resistance and pressure of the body fluid; and a control member, operable to control the flow of the body fluid from the first tissue/organ to the second tissue/organ of the subject, wherein the control member comprises an inflatable balloon and an inflator in fluid communication with the inflatable balloon, wherein the inflator is operable to selectively inflate or deflate the inflated balloon, and the inflatable balloon is disposed within the main body such that the level of inflation and/or deflation of the inflatable balloon controls the flow of the body fluid into and/or from the lumen.

2. The flow control device of claim 1, wherein the body fluid is the pancreatic juice, the first tissue/organ is the pancreas and the second tissue/organ is the duodenum, wherein the distal end of the first fluid channel is adapted to be connected to the pancreatic duct thereby establishing the fluid communication between the lumen and the pancreas.

3. The flow control device of claim 1, wherein the first fluid channel has a plurality of first openings disposed on a portion of the surface of the first fluid channel.

4. The flow control device of claim 1, wherein the second fluid channel has a plurality of second openings disposed on a portion of the surface of the second fluid channel.

5. The flow control device of claim 1, wherein the distal end of the first fluid channel has a diameter less than the diameter of the distal end of the second fluid channel.

6. The flow control device of claim 1, further comprising at least one multi-way valve that comprises at least two nozzles.

7. The flow control device of claim 6, wherein the multi-way valve is a three-way valve that comprises three nozzles.

8. The flow control device of claim 6, wherein the multi-way valve is operable to establish the fluid communication between any two of the lumen, the first fluid channel, the second fluid channel and the detection member.

9. The flow control device of claim 1, wherein the flow control device further comprises a third fluid channel operable to be in fluid communication with the lumen and the detection member.

10. The flow control device of claim 1, wherein the detection member comprises a plurality of sensors disposed within the first fluid channel, the second fluid channel and/or the lumen.

11. The flow control device of claim 10, wherein the plurality of sensors comprise thin-film transistors.

12. The flow control device of claim 1, further comprising at least one tab fixed to the outer surface of the first fluid channel, the outer surface of the second fluid channel, or both.

13. The flow control device of claim 1, further comprising at least one flap extended from the outer surface of the first fluid channel and/or the outer surface of the second fluid channel.

14. A flow control system for controlling the flow of a body fluid from a first tissue/organ to a second tissue/organ of a subject, comprising, the flow control device of claim 1;

a computing device in operative connection with the flow control device, and configured to allow the control member to control the flow of the body fluid from the first tissue/organ to the second tissue/organ of the subject based on a detection result obtained by the detection member.

15. The flow control system of claim 14, wherein the body fluid is the pancreatic juice, the first tissue/organ is the pancreas and the second tissue/organ is the duodenum, wherein the distal end of the first fluid channel is adapted to be connected to the pancreatic duct thereby establishing the fluid communication between the lumen and the pancreas.

16. The flow control system of claim 14, further comprising a wireless communication module for establishing a communication connection between the flow control device and the computing device.

17. The flow control system of claim 14, wherein the computing device comprises a storage unit for storing a set of data of the relationship between an injury level of the first tissue/organ and at least one parameter selected from the group consisting of the flow rate, velocity, flow resistance and pressure of the body fluid; and the control member is operable to control the flow of the body fluid from the first tissue/organ to the second tissue/organ of the subject based on the detection result obtained by the detection member and the set of data stored in the storage unit.

18. The flow control system of claim 14, wherein the computing device comprises an analysis unit for analyzing the detection result obtained by the detection member; and the control member is operable to control the flow of the body fluid from the first tissue/organ to the second tissue/organ of the subject based on the analysis result obtained by the analysis unit.

19. The flow control system of claim 14, wherein the computing device comprises a determination unit for making a determination based on the detection result obtained by the detection member; and the control member is operable to control the flow of the body fluid from the first tissue/organ to the second tissue/organ of the subject based on the determination result obtained by the determination unit.

20. The flow control system of claim 14, wherein the computing device comprises, (1) a storage unit for storing a set of data of the relationship between an injury level of the first tissue/organ and at least one parameter selected from the group consisting of the flow rate, velocity, flow resistance and pressure of the body fluid;

(2) an analysis unit for analyzing the detection result obtained by the detection member based on the set of data stored in the storage unit; and (3) a determination unit for making a determination based on the analysis result obtained by the analysis unit; and the control member is operable to control the flow of the body fluid from the first tissue/organ to the second tissue/organ of the subject based on the determination result obtained by the determination unit.

21. A method for inducing mild inflammation or microinjury in a first and/or second tissue/organ of a subject by controlling the flow of a body fluid from the first tissue/organ to the second tissue/organ of the subject comprising the steps of, (a) arranging the flow control device of claim 1, such that, (a-1) the distal end of the first fluid channel locates in adjacent to the exit of the first tissue/organ, thereby allowing the flow of the body fluid from the first tissue/organ into the lumen via the first fluid channel; and (a-2) the distal end of the second fluid channel is connected to an opening of the second tissue/organ, thereby allowing the flow of the body fluid from the lumen into the second tissue/organ via the second fluid channel;

(b) detecting at least one parameter selected from the group consisting of: the flow rate, velocity, flow resistance and pressure of the body fluid by the detection member; and (c) controlling the flow of the body fluid by the control member such that at least one of the flow rate, velocity, flow resistance and pressure of the body fluid is adjusted to an extent sufficient to cause the mild inflammation or microinjury of the first and/or second tissue/organ of the subject.

22. The method of claim 21, wherein the body fluid is the pancreatic juice, the first tissue/organ is the pancreas and the second tissue/organ is the duodenum, wherein the distal end of the first fluid channel is connected to the pancreatic duct thereby establishing the fluid communication between the lumen and the pancreas.

23. The method of claim 22, wherein the subject is a pig or a human; and in the step (c) the flow of the pancreatic juice from the pancreas is controlled to an extent such that the pressure within the pancreatic duct is about 10-50 cmH$_2$O.

24. The method of claim 21, further comprising, (d) collecting a pancreatic juice and/or blood sample from the subject, and detecting the level of pancreatic lipase, pancreatic amylase, glucose, insulin or C-peptide of the subject.

25. The method of claim 24, wherein the step (c) further comprises adjusting at least one of the flow rate, velocity, flow resistance and pressure of the based on the detection result of the step (d).

* * * * *